United States Patent [19]

Yokoyama et al.

[11] Patent Number: 4,654,337

[45] Date of Patent: Mar. 31, 1987

[54] PERFLUORO-1-AZATRICYCLIC AMINE COMPOUNDS USEFUL AS BLOOD SUBSTITUTES OR IN INFUSION FLUIDS

[75] Inventors: Kazumasa Yokoyama, Toyonaka; Chikara Fukaya, Osaka; Yoshio Tsuda, Takarazuka; Taizo Ono, Osaka; Yoshio Arakawa, Suita; Yoshihisa Inoue, Kyoto; Youichiro Naito, Hirakata; Tadakazu Suyama, Kyoto, all of Japan

[73] Assignee: The Green Cross Corporation, Osaka, Japan

[21] Appl. No.: 751,880

[22] Filed: Jul. 5, 1985

Related U.S. Application Data

[62] Division of Ser. No. 505,322, Jun. 17, 1983, Pat. No. 4,542,147.

[30] Foreign Application Priority Data

| Aug. 7, 1982 | [JP] | Japan | 57-137663 |
| Aug. 7, 1982 | [JP] | Japan | 57-137664 |
| Aug. 7, 1982 | [JP] | Japan | 57-137665 |

[51] Int. Cl.$^4$ .................. C07D 223/00; A61K 31/435
[52] U.S. Cl. ..................................... 514/214; 514/294; 514/832; 514/833; 540/581; 540/477
[58] Field of Search ................ 540/581, 477; 514/214, 514/294, 832, 833

[56] References Cited

U.S. PATENT DOCUMENTS

| 4,186,253 | 1/1980 | Yokoyama et al. | 514/227 X |
| 4,425,347 | 1/1984 | Yokoyama et al. | 514/832 X |
| 4,526,969 | 7/1985 | Yokoyama et al. | 260/245.7 X |
| 4,562,183 | 12/1985 | Tatlow et al. | 514/214 |

Primary Examiner—Donald G. Daus
Assistant Examiner—William A. Teoli, Jr.
Attorney, Agent, or Firm—Cushman, Darby & Cushman

[57] ABSTRACT

A novel compound of the formula,

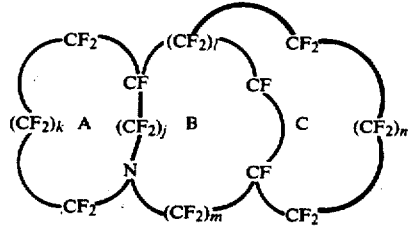

wherein k is zero or an integer of 1 to 2, j is an integer of from 1 or 3, l and m are each zero or an integer of from 1 to 3, and n is an integer of from 1 to 4, the rings A, B and C being optionally substituted with at least one trifluoromethyl group or tetrafluoroethyl group is prepared by reacting the perhydro compound corresponding thereto with fluorine. The compound is useful as a material capable of carrying oxygen in an aqueous emulsion for lifesaving a patient suffering from massive hemorrhage and for preserving internal organs in transplantation.

21 Claims, No Drawings

PERFLUORO-1-AZATRICYCLIC AMINE COMPOUNDS USEFUL AS BLOOD SUBSTITUTES OR IN INFUSION FLUIDS

This is a division of application Ser. No. 505,322 filed June 17, 1983, now U.S. Pat. No. 4,542,147.

This invention relates to novel perfluorotricyclic amine compound useful as an oxygen carrier in an artificial blood or in an infusion fluid.

More particularly, it relates to a perfluoro-1-azatricyclic amine compound represented by the general formula

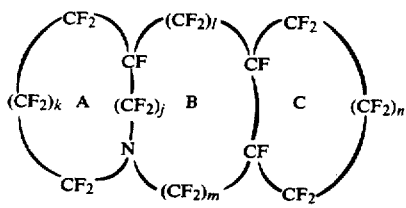

wherein k is zero or an integer of 1 or 2, j is an integer of from 1 to 3, l and m are each zero or an integer of from 1 to 3, and n is an integer of from 1 to 4, the rings A, B and C being optionally substituted with at least one trifluoromethyl or pentafluoroethyl group.

Regarding the general formula (I), it is preferable that the ring A is selected from five- to eight-membered rings, the ring B from five- to eight-membered rings, and the ring C from five- to eight-membered rings. The total number of the carbon atoms contained in the compound of formula (I) is preferably from 9 to 12.

In detail, the first series of the present perfluoro-1-azatricyclic amine compounds without optional substitutent of —CF$_3$ or —C$_2$F$_5$ is represented by the formula,

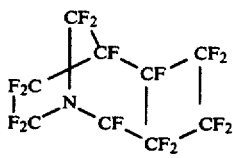

The compound of the above formula may have the substituent(s), and the preferable total number of the compound being 9 to 11.

The second series is also represented by the formula,

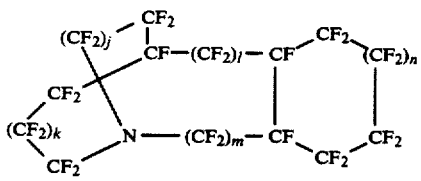

wherein k, j, l, m and n are each zero or an integer of 1, 2 or 3; provided that k and j are not simultaneously zero.

The compound may have one trifluoromethyl group as substituent and its total number of carbon atoms is preferably 10 to 12 in case of no substituent and 11 in case of the presence of the substituent.

The third series is also represented by the formula,

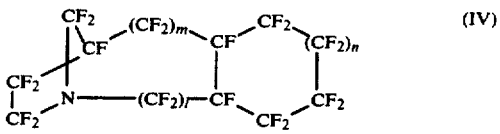

wherein n, l and m are each zero or an integer of from 1 to 3, provided that any one of the l, m and n is an integer of from 1 to 3.

The compound may have one trifluoromethyl group as substituent and its total number of carbon atoms is preferably 10 to 12 in case of no substituent and 11 in case of the presence of the substituent.

The compound of formula (I) can be prepared by fluorinating a perhydro-compound corresponding to the compound of formula (I). The methods of fluorination include, for example, a direct fluorination, a fluorination by use of cobalt trifluoride, and an electro chemical fluorination.

The preparation of the compound of formula (I) of this invention is preferably performed by the electrochemical fluorination method. This is performed, for example, by mixing anhydrous hydrogen fluoride and the perhydro-compound used as the starting compound in an electrolytic cell and subjecting the resulting solution to electrolysis. The voltage, the current density at the anode, and the temperature of electrolytic solution are normally 3–8 V, 0.1–3 A/dm$^2$ and 4–12° C., respectively.

The compound of formula (I) thus formed was drained from the bottom of the cell, being insoluble in anhydrous hydrogen fluoride.

The isolation and purification of the compound from the drained product are carried out, for example, by adding a mixture of equal volumes of an aqueous caustic alkaline solution and an amine compound to the drained product and refluxing to decompose partially fluorinated compounds. After cooled, the lowermost layer containing the desired compound of formula (I) is separated, washed with an aqueous acetone solution containing a suitable amount of potassium iodide to remove perfluoroalkyl nitrogen fluorides, and subjected to fractional distillation to obtain the fraction of the desired compound of formula (I).

Since the compound of the formula (I) of this invention can not only dissolve a large amount of oxygen, and is chemically and biologically inert, but also it can be excreted rapidly from the body, it can form, for example, an aqueous emulsion containing 5 to 50, preferably 10–40, %(W/V) of the compuond of formula (I) to be used as an oxygen carrier in an artificial blood or in an infusion liquid for men and other mammals such as dogs, cats, cattle, mice, rats and guinea pigs.

The symbol "%(W/V)" referred to herein mean the amount of the material by weight (gram) based on 100 ml of the resulting emulsion.

In the preparation of the emulsion mentioned above, there used, as an emulsifier, a nonionic surfactant and/or phospholipids in an added amount of 1 to 5% (W/V).

As the medium for the emulsion, a physiologically acceptable aqueous solution is employed. If necessary, there may be added thereto such materials as glycerol to provide the desired isotonicity, and such plasma expanders as HES or dextran to regulate the colloid osmotic pressure of the emulsion.

The emulsion can be prepared by mixing the above-mentioned ingredients and homogenizing the mixture by means of, for example, a high-pressure jet type homogenizer until the particle diameters become 0.05 to 0.3 μm, preferably less than 0.2 μm.

The perhydro-compounds (starting compounds) corresponding to the compounds of formula (I) are substantially known already.

EXAMPLE 1

Into an electrolytic cell made of Monel metal with an inner volume of 1.5 l, which is provided with electrode plates (six plates as anode and seven plates as cathode) made of nickel (purity: 99.6% or higher) arranged alternately with an inter-electrode distance of 1.7-2.0 mm, the effective anode surface area being 10.5 dm², and with a reflux condenser made of copper at the upper part of the cell, was introduced 1.2 l of anhydrous hydrogen fluoride, and trace amounts of impurities present in the system (moisture and sulfuric acid) were removed by preliminary electrolysis. Then, 1.0 mol (137 g) of 1-azatricyclo[5,2,1,0,$^{2,6}$]decane was dissolved into the anhydrous hydrogen fluoride, and electrolysis was carried out, while introducing helium gas from the bottom of the cell at a rate of 100 ml/min., under the conditions of anode current density of 0.4-2.0 A/dm², voltage of 5-9 V and solution temperature 7-12° C., until the ampere-hours amounted to 900. Hydrogen fluoride was added at a rate of 250 ml per 24 hours during the electrolysis. No attempt was made to collect volatile products formed by a bond breaking reaction, which would give more yields of the desired product. After completion of the electrolysis, fluorocarbons in the lower layer in the cell was drained through the bottom of the cell, weighed 252 g (58% yield).

To the fluorocarbons thus separated, were added equal volumes of 70% aqueous potassium hydroxide solution and diisobutylamine, and the resulting mixture was refluxed from about five days. The reaction mixture was then cooled in an ice bath, and filtered by suction. The perfluoro-compounds sedimented in the lowermost layer were separated in a separatory funnel, washed successively with diluted suluric acid, concentrated sulfuric acid, saturated aqueous sodium hydrogen carbonate solution, 90% aqueous actone solution containing 3% of potassium iodide, and water to yield 100 g of a transparent perfluoro-compound. The thus obtained perfluoro-compound free from contaminants containing protons was distilled on a fractional distillation apparatus equipped with a spinning band column to afford 33 g (7% yield) of the desired product boiling at 120-130° C. This product was collected, purified, and then analyzed by infrared absorption spectrometry, $^{19}$F-nuclear magnetic resonance spectrometory and mass spectrometory, and was confirmed to be the objective compound, perfluoro-1-azatricyclo[5,2,1,0$^{2,6}$]decane of which chemical structure was shown in Table 1 as compound No. 1.

EXAMPLES 2-68

A series of other perfluoro-1-azatricyclic amine compounds having the formula (II) and (IV) was synthesized from the corresponding perhydro-1-azatricyclic amine compounds and purified in the same manner as that described above and each product was confirmed to be the objective compound upon analysis by infrared absorption spectrometory, $^{19}$F-nuclear magnetic resonance spectrometory and mass spectrometory.

The structural formula and the boiling point of each of the objective compounds and the starting compounds are shown in the Table 1. The symbol "F-" in the structural formula indicates that the compound is perfluorinated. For example, the formula

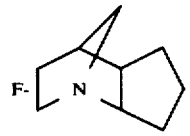

indicates in its exact meaning the formula

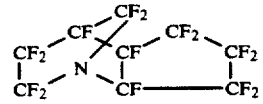

TABLE 1

| Example No. | Starting compound | Objective compound | Boiling pt. (°C.) |
|---|---|---|---|
| 1 | 1-Azatricyclo [5,2,1,0$^{2,6}$]decane | | 120-130 |
| 2 | 3-Methyl-1-azatricyclo [5,2,1,0$^{2,6}$]decane | | 143-154 |
| 3 | 4-Methyl-1-azatricyclo [5,2,1,0$^{2,6}$]decane | | 143-153 |
| 4 | 5-Methyl-1-azatricyclo [5,2,1,0$^{2,6}$]decane | | 143-153 |
| 5 | 8-Methyl-1-azatricyclo [5,2,1,0$^{2,6}$]decane | | 143-153 |
| 6 | 9-Methyl-1-azatricyclo [5,2,1,0$^{2,6}$]decane | | 143-153 |

TABLE 1-continued

| Example No. | Starting compound | Objective compound | Boiling pt. (°C.) |
|---|---|---|---|
| 7 | 10-Methyl-1-azatricyclo[5,2,1,0²,⁶]decane | | 143–154 |
| 8 | 3-Ethyl-1-azatricyclo[5,2,1,0²,⁶]decane | | 157–168 |
| 9 | 4-Ethyl-1-azatricyclo[5,2,1,0²,⁶]decane | | 156–168 |
| 10 | 5-Ethyl-1-azatricyclo[5,2,1,0²,⁶]decane | | 157–168 |
| 11 | 8-Ethyl-1-azatricyclo[5,2,1,0²,⁶]decane | | 157–168 |
| 12 | 9-Ethyl-1-azatricyclo[5,2,1,0²,⁶]decane | | 157–168 |
| 13 | 10-Ethyl-1-azatricyclo[5,2,1,0²,⁶]decane | | 158–168 |
| 14 | 3,4-Dimethyl-1-azatricyclo[5,2,1,0²,⁶]decane | | 157–168 |
| 15 | 3,5-Dimethyl-1-azatricyclo[5,2,1,0²,⁶]decane | | 158–168 |
| 16 | 3,8-Dimethyl-1-azatricyclo[5,2,1,0²,⁶]decane | | 158–168 |
| 17 | 3,9-Dimethyl-1-azatricyclo[5,2,1,0²,⁶]decane | | 158–167 |
| 18 | 3,10-Dimethyl-1-azatricyclo[5,2,1,0²,⁶]decane | | 157–168 |
| 19 | 4,5-Dimethyl-1-azatricyclo[5,2,1,0²,⁶]decane | | 157–168 |
| 20 | 4,8-Dimethyl-1-azatricyclo[5,2,1,0²,⁶]decane | | 157–167 |
| 21 | 4,9-Dimethyl-1-azatricyclo[5,2,1,0²,⁶]decane | | 157–168 |
| 22 | 4,10-Dimethyl-1-azatricyclo[5,2,1,0²,⁶]decane | | 157–167 |
| 23 | 5,8-Dimethyl-1-azatricyclo[5,2,1,0²,⁶]decane | | 157–167 |
| 24 | 5,9-Dimethyl-1-azatricyclo[5,2,1,0²,⁶]decane | | 157–168 |

TABLE 1-continued

| Example No. | Starting compound | Objective compound | Boiling pt. (°C.) |
|---|---|---|---|
| 25 | 5,10-Dimethyl-1-azatricyclo[5,2,1,0$^{2,6}$]decane | | 157–167 |
| 26 | 8,9-Dimethyl-1-azatricyclo[5,2,1,0$^{2,6}$]decane | | 158–167 |
| 27 | 8,10-Dimethyl-1-azatricyclo[5,2,1,0$^{2,6}$]decane | | 157–168 |
| 28 | 9,10-Dimethyl-1-azatricyclo[5,2,1,0$^{2,6}$]decane | | 157–167 |
| 29 | 1-Azatricyclo[6,2,1,0$^{2,7}$]undecane | | 143–153 |
| 30 | 3-Methyl-1-azatricyclo[6,2,1,0$^{2,7}$]undecane | | 156–167 |
| 31 | 4-Methyl-1-azatricyclo[6,2,1,0$^{2,7}$]undecane | | 157–166 |
| 32 | 5-Methyl-1-azatricyclo[6,2,1,0$^{2,7}$]undecane | | 157–166 |
| 33 | 6-Methyl-1-azatricyclo[6,2,1,0$^{2,7}$]undecane | | 156–166 |
| 34 | 9-Methyl-1-azatricyclo[6,2,1,0$^{2,7}$]undecane | | 156–166 |
| 35 | 10-Methyl-1-azatricyclo[6,2,1,0$^{2,7}$]undecane | | 156–167 |
| 36 | 11-Methyl-1-azatricyclo[6,2,1,0$^{2,7}$]undecane | | 156–166 |
| 37 | 1-Azatricyclo[6,2,1,0$^{2,6}$]undecane | | 143–154 |
| 38 | 3-Methyl-1-azatricyclo[6,2,1,0$^{2,6}$]undecane | | 156–166 |
| 39 | 4-Methyl-1-azatricyclo[6,2,1,0$^{2,6}$]undecane | | 156–167 |
| 40 | 5-Methyl-1-azatricyclo[6,2,1,0$^{2,6}$]undecane | | 156–167 |
| 41 | 7-Methyl-1-azatricyclo[6,2,1,0$^{2,6}$]undecane | | 156–167 |
| 42 | 9-Methyl-1-azatricyclo[6,2,1,0$^{2,6}$]undecane | | 156–166 |

TABLE 1-continued

| Example No. | Starting compound | Objective compound | Boiling pt. (°C.) |
|---|---|---|---|
| 43 | 10-Methyl-1-azatricyclo[6,2,1,0²,⁶]undecane | | 156–167 |
| 44 | 11-Methyl-1-azatricyclo[6,2,1,0²,⁶]undecane | | 156–168 |
| 45 | 1-Azatricyclo[6,2,1,0³,⁷]undecane | | 145–154 |
| 46 | 2-Methyl-1-azatricyclo[6,2,1,0³,⁷]undecane | | 156–168 |
| 47 | 4-Methyl-1-azatricyclo[6,2,1,0³,⁷]undecane | | 156–167 |
| 48 | 5-Methyl-1-azatricyclo[6,2,1,0³,⁷]undecane | | 156–167 |
| 49 | 6-Methyl-1-azatricyclo[6,2,1,0³,⁷]undecane | | 156–166 |
| 50 | 9-Methyl-1-azatricyclo[6,2,1,0³,⁷]undecane | | 157–167 |
| 51 | 10-Methyl-1-azatricyclo[6,2,1,0³,⁷]undecane | | 157–167 |
| 52 | 11-Methyl-1-azatricyclo[6,2,1,0³,⁷]undecane | | 156–167 |

TABLE 1-continued

| Example No. | Starting compound | Objective compound | Boiling pt. (°C.) |
|---|---|---|---|
| 53 | 1-Azatricyclo[7,2,1,0²,⁶]dodecane | | 156–166 |
| 54 | 1-Azatricyclo[7,2,1,0²,⁷]dodecane | | 156–167 |
| 55 | 1-Azatricyclo[7,2,1,0²,⁸]dodecane | | 156–166 |
| 56 | 1-Azatricyclo[7,2,1,0³,⁷]dodecane | | 155–165 |
| 57 | 1-Azatricyclo[7,2,1,0³,⁸]dodecane | | 156–166 |
| 58 | 1-Azatricyclo[7,2,1,0⁴,⁸]dodecane | | 155–166 |
| 59 | 1-Azatricyclo[8,2,1,0²,⁶]tridecane | | 158–177 |
| 60 | 1-Azatricyclo[8,2,1,0²,⁷]tridecane | | 167–177 |
| 61 | 1-Azatricyclo[8,2,1,0²,⁸]tridecane | | 167–178 |
| 62 | 1-Azatricyclo[8,2,1,0²,⁹]tridecane | | 166–178 |

TABLE 1-continued

| Example No. | Starting compound | Objective compound | Boiling pt. (°C.) |
|---|---|---|---|
| 63 | 1-Azatricyclo [8,2,1,0$^{3,7}$] tridecane | | 167–178 |
| 64 | 1-Azatricyclo [8,2,1,0$^{3,8}$] tridecane | | 166–177 |
| 65 | 1-Azatricyclo [8,2,1,0$^{3,9}$] tridecane | | 167–177 |
| 66 | 1-Azatricyclo [8,2,1,0$^{4,8}$] tridecane | | 167–178 |
| 67 | 1-Azatricyclo [8,2,1,0$^{4,9}$] tridecane | | 167–177 |
| 68 | 1-Azatricyclo [8,2,1,0$^{5,9}$] tridecane | | 166–176 |

EXAMPLES 69–107

A series of perfluorotricyclic amine compounds of the formula (IV) was synthesized, purified and confirmed to be the objective compound in the same manner as in Example 1.

The structural formula and the boiling point of each of the objective compounds is shown in Table 2. The symbol "F-" in the structural formula indicates that the compound is perfluorinated. For example, the formula

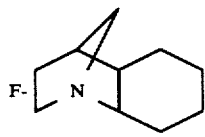

indicates in its exact meaning the formula

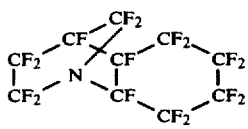

TABLE 2

| Example No. | Starting compound | Formula of objective compound | Boiling pt. (°C.) |
|---|---|---|---|
| 69 | 1-Azatricyclo [5,3,1,0$^{2,6}$]undecane | | 143–152 |
| 70 | 3-Methyl-1-azatricyclo[5,3,1,0$^{2,6}$] undecane | | 156–167 |
| 71 | 4-Methyl-1-azatricyclo[5,3,1,0$^{2,6}$] undecane | | 156–167 |
| 72 | 5-Methyl-1-azatricyclo[5,3,1,0$^{2,6}$] undecane | | 156–168 |
| 73 | 8-Methyl-1-azatricyclo[5,3,1,0$^{2,6}$] undecane | | 156–166 |
| 74 | 9-Methyl-1-azatricyclo[5,3,1,0$^{2,6}$] undecane | | 156–167 |

TABLE 2-continued

| Example No. | Starting compound | Formula of objective compound | Boiling pt. (°C.) |
|---|---|---|---|
| 75 | 10-Methyl-1-azatricyclo[5,3,1,0$^{2,6}$]undecane | | 155–166 |
| 76 | 1-Azatricyclo[6,3,1,0$^{2,7}$]dodecane | | 154–166 |
| 77 | 1-Azatricyclo[6,3,1,0$^{2,6}$]dodecane | | 155–166 |
| 78 | 1-Azatricyclo[6,3,1,0$^{3,7}$]dodecane | | 155–166 |
| 79 | 1-Azatricyclo[7,3,1,0$^{2,6}$]tridecane | | 167–177 |
| 80 | 1-Azatricyclo[7,3,1,0$^{2,7}$]tridecane | | 167–177 |
| 81 | 1-Azatricyclo[7,3,1,0$^{2,8}$]tridecane | | 167–177 |
| 82 | 1-Azatricyclo[7,3,1,0$^{3,7}$]tridecane | | 166–176 |
| 83 | 1-Azatricyclo[7,3,1,0$^{3,8}$]tridecane | | 167–177 |
| 84 | 1-Azatricyclo[7,3,1,0$^{4,8}$]tridecane | | 167–177 |
| 85 | 1-Azatricyclo[5,4,1,0$^{2,6}$]dodecane | | 155–166 |
| 86 | 1-Azatricyclo[6,4,1,0$^{2,7}$]tridecane | | 167–178 |
| 87 | 1-Azatricyclo[6,4,1,0$^{2,6}$]tridecane | | 167–177 |
| 88 | 1-Azatricyclo[6,4,1,0$^{3,7}$]tridecane | | 167–177 |
| 89 | 1-Azatricyclo[5,2,2,0$^{2,6}$]undecane | | 144–155 |

TABLE 2-continued

| Example No. | Starting compound | Formula of objective compound | Boiling pt. (°C.) |
|---|---|---|---|
| 90 | 3-Methyl-1-azatricyclo[5,2,2,0²,⁶]undecane | | 156–167 |
| 91 | 4-Methyl-1-azatricyclo[5,2,2,0²,⁶]undecane | | 155–166 |
| 92 | 5-Methyl-1-azatricyclo[5,2,2,0²,⁶]undecane | | 156–167 |
| 93 | 8-Methyl-1-azatricyclo[5,2,2,0²,⁶]undecane | | 156–166 |
| 94 | 9-Methyl-1-azatricyclo[5,2,2,0²,⁶]undecane | | 156–166 |
| 95 | 1-Azatricyclo[6,2,2,0²,⁷]dodecane | | 155–165 |
| 96 | 1-Azatricyclo[6,2,2,0²,⁶]dodecane | | 156–166 |
| 97 | 1-Azatricyclo[6,2,2,0³,⁷]dodecane | | 156–166 |
| 98 | 1-Azatricyclo[7,2,2,0²,⁶]tridecane | | 157–166 |
| 99 | 1-Azatricyclo[7,2,2,0²,⁷]tridecane | | 156–167 |
| 100 | 1-Azatricyclo[7,2,2,0²,⁸]tridecane | | 155–167 |
| 101 | 1-Azatricyclo[7,2,2,0³,⁷]tridecane | | 156–167 |
| 102 | 1-Azatricyclo[7,2,2,0³,⁸]tridecane | | 156–166 |
| 103 | 1-Azatricyclo[7,2,2,0⁴,⁸]tridecane | | 154–166 |
| 104 | 1-Azatricyclo[6,3,2,0²,⁶]tridecane | | 156–166 |
| 105 | 1-Azatricyclo[6,3,2,0²,⁷]tridecane | | 156–166 |

TABLE 2-continued

| Example No. | Starting compound | Formula of objective compound | Boiling pt. (°C.) |
|---|---|---|---|
| 106 | 1-Azatricyclo [6,3,2,0$^{3,7}$]tridecane | | 156–167 |
| 107 | 1-Azatricyclo [5,3,3,0$^{2,6}$] tridecane | | 155–165 |

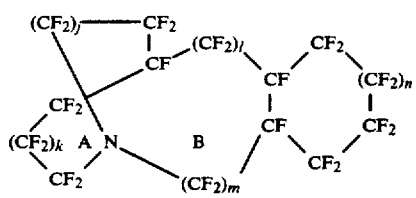

What is claimed is:

1. A perfluoro-1-azatricyclic amine compound represented by the formula:

$$(CF_2)_j\text{—}CF_2$$
$$\underset{(CF_2)_k}{\overset{CF_2}{\diagup}}\overset{CF}{\underset{A}{\diagdown}}\overset{(CF_2)_l}{\underset{N}{\diagup}}\overset{CF_2}{\underset{B}{\diagdown}}\overset{CF}{\underset{(CF_2)_m}{\diagup}}\overset{CF_2}{\underset{CF_2}{\diagdown}}\overset{(CF_2)_n}{\underset{CF_2}{\diagup}}$$

wherein j, k, l and m ae each an integer of from zero to 3 so as to make one of the rings A and B to be 6 membered and the other 7 or more membered; n is zero, or 1; any one fluorine being optionally replaced by one trifluoromethyl group.

2. A perfluoro-1-azatricyclic amine compound according to claim 1, wherein j is 1, k is 0, and l and m is 2.

3. A perfluoro-1-azatricyclic amine compound of claim 2 which is 1-azatricyclo[7,3,1,0$^{2,6}$]tridecane.

4. A perfluoro-1-azatricyclic amine compound of claim 2 which is 1-azatricyclo[7,3,1,0$^{3,7}$]tridecane.

5. A perfluoro-1-azatricyclic amine compound of claim 2, which is 1-azatricyclo[7,3,1,0$^{4,8}$]tridecane.

6. A perfluoro-1-azatricyclic amine compound according to claim 1, wherein j is zero, k is 1, and l plus m is 1 or 2.

7. A perfluoro-1-azatricyclic amine compound of claim 6, which is 1-azatricyclo[6,2,2,0$^{2,6}$]dodecane.

8. A perfluoro-1-azatricyclic amine compound of claim 6, which is 1-azatricyclo[6,2,2,0$^{2,7}$]dodecane.

9. A perfluoro-1-azatricyclic amine compound of claim 6, which is 1-azatricyclo[7,2,2,0$^{2,6}$]tridecane.

10. A perfluoro-1-azatricyclic amine compound of claim 6, which is 1-azatricyclo[7,2,2,0$^{2,7}$]tridecane.

11. A perfluoro-1-azatricyclic amine compound of claim 6, which is 1-azatricyclo[7,2,2,0$^{3,7}$]tridecane.

12. A perfluoro-1-azatricyclic amine compound of claim 6, which is 1-azatricyclo[7,2,2,0$^{3,8}$]tridecane.

13. A perfluoro-1-azatricyclic amine compound according to claim 6, which is 1-azatricyclo[7,2,2,0$^{4,8}$]tridecane.

14. A perfluoro-1-azatricyclic amine compound according to claim 1, wherein j is 2, k is zero, and l plus m is 1.

15. A perfluoro-1-azatricyclic amine compound of claim 14, which is 1-azatricyclo[6,4,1,0$^{2,6}$]tridecane.

16. A perfluoro-1-azatricyclic amine compound of claim 14, which is 1-azatricyclo[6,4,1,0$^{3,7}$]tridecane.

17. A perfluoro-1-azatricyclic amine compound according to claim 1, wherein j and k are each 1, and l and m are each zero.

18. A perfluoro-1-azatricyclic amine compound of claim 17, which is 1-azatricyclo6,3,2,0$^{2,7}$]tridecane.

19. A composition for use as a blood substitute or infusion fluid which composition is an aqueous emulsion of a compound of the formula given and defined in claim 1.

20. A compostion according to claim 19, which contains from 5 to 50% (W/V) of the compound of the formula given and defined in claim 11.

21. A composition according to claim 19, which contains, as emulsifier, a nonionic surfactant and/or phospholipid.

* * * * *

UNITED STATES PATENT AND TRADEMARK OFFICE
CERTIFICATE OF CORRECTION

PATENT NO. : 4,654,337
DATED : March 31, 1987
INVENTOR(S) : YOKOYAMA ET AL

It is certified that error appears in the above-identified patent and that said Letters Patent is hereby corrected as shown below:

IN THE ABSTRACT, replace the formula by the following:

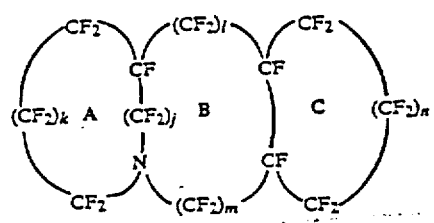

Signed and Sealed this

Fifth Day of July, 1988

Attest:

DONALD J. QUIGG

Attesting Officer

Commissioner of Patents and Trademarks